United States Patent
Carnevale

(10) Patent No.: US 7,334,896 B2
(45) Date of Patent: Feb. 26, 2008

(54) GRAYSCALE REDISTRIBUTION SYSTEM TO IMPROVE RETINAL IMAGING BY REDUCING THE EFFECT OF A HIGHLY REFLECTIVE OPTIC NERVE

(76) Inventor: Matthew Carnevale, 26 Foss St., Medford, MA (US) 02155

( * ) Notice: Subject to any disclaimer, the term of this patent is extended or adjusted under 35 U.S.C. 154(b) by 315 days.

(21) Appl. No.: 11/241,521

(22) Filed: Sep. 30, 2005

(65) Prior Publication Data

US 2007/0076169 A1    Apr. 5, 2007

(51) Int. Cl.
  *A61B 3/00*   (2006.01)
  *H04N 5/222*  (2006.01)
  *G06K 9/00*   (2006.01)
(52) U.S. Cl. .................... 351/246; 348/371; 382/117
(58) Field of Classification Search ................ 351/246
  See application file for complete search history.

(56) References Cited

U.S. PATENT DOCUMENTS

2004/0208343 A1* 10/2004 Golden et al. .............. 382/110
2005/0232506 A1* 10/2005 Smith et al. ................ 382/254

* cited by examiner

*Primary Examiner*—Scott J. Sugarman
*Assistant Examiner*—DaWayne A Pinkney
(74) *Attorney, Agent, or Firm*—Robert K. Tendler

(57) ABSTRACT

A system is provided to improve retinal camera picture quality by providing a user-variable transfer function for each pixel that results in redistributing grayscale values to solve the problem of saturation caused by highly reflective retinal objects. The result is the ability to capture both optic nerve and retina detail in a single picture. The darker retina is brightened to permit observing retinal detail using the redistributed grayscale values, while preserving optic nerve detail. Those pixels experiencing high-intensity reflections are properly exposed to prevent saturation, while outputs of low-intensity pixels associated with the darker regions are intensified, in one embodiment in accordance with an adjustable Bezier curve. The result is that one can obtain retinal details previously flooded out by the reflections from the optic nerve while at the same time offering optic nerve detail. In one embodiment the redistributed grayscale values are optimized for each color plane to provide color-corrected images matching those associated with film cameras.

24 Claims, 8 Drawing Sheets

GRAYSCALE REDISTRIBUTION SYSTEM TO IMPROVE RETINAL IMAGING BY REDUCING THE EFFECT OF A HIGHLY REFLECTIVE OPTIC NERVE

FIELD OF THE INVENTION

This invention relates to retinal cameras and more particularly to a system for eliminating the effects of a highly reflective optic nerve so that detail of both the optic nerve and detail of the surrounding retinal material are viewable.

BACKGROUND OF THE INVENTION

In retinal imaging, one seeks to obtain photographs of the detail of the optic nerve and the surrounding retinal material that heretofore has been captured on film.

A constant problem in retinal imaging is the fact that the optic nerve, which is basically where all of the nerve bundles go back to the brain, is very reflective. When one fires a strobe into the eye to illuminate the retina, the optic nerve tends to throw large amounts of light back at the camera, which shows up as a bright blotch at the position where the optic nerve is attached to the retina. The rest of the detail of the retina that one wants to see, especially at the periphery, is very dark. The result of photographing the retina utilizing high-power strobe pulse illumination is a very high-contrast image where the darker regions are drowned out by the high reflectivity of the optic nerve.

More importantly, the optic nerves of the darker-skinned races, including the Negroid and Hispanic races, are in general more highly reflective than white or Caucasian races, making retinal imaging even more difficult. It is noted that people of darker complexion have darker retinas because the pigment of the retina is darker.

When taking retinal images, one has to inject enough light to illuminate the dark areas. However, if one increases the output of the xenon strobe normally used, one simply drowns out the optic nerve detail because of its high reflectivity.

In the past, in order to obtain images of the detail of the optic nerve as well as images of the retina, one had to take numbers of photographs, each with different light outputs or different F stops on the camera. With multiple pictures one needs multiple strobe pulses, with each strobe pulse injecting energy into the eye. This causes pain and is very uncomfortable for the patient. What this means is that a patient may have to endure a number of 100 watt-second pulses discharged into the eye. It is therefore desirable to be able to eliminate the requirement for multiple exposures.

However, the problem is not so much seeing the remainder of the optic nerve but dealing with the high reflections where the optic nerve is attached to the retina that visually resembles a hole in the back of the eye. As will be appreciated, the optic nerve is always on the nasal side of the eye and appears as an offset bright hole. On the other hand, the retina has blood vessels and arteries that stretch out across the eye including smaller capillaries that branch off. In general, the vascular structure forms a circular pattern. At the center of vision, which is called the macula, there are no blood vessels and therefore it is completely devoid of blood vessel structure.

It is noted that in addition to the optic nerve, pathology can be highly reflective as well. High reflections can come from a scar, tumor or growth, the reflections from which will saturate the camera with the introduction of a pulse from the xenon strobe.

As mentioned hereinabove, one technique to eliminate the problems of being able to view the structure of the eye is to have multiple photographs, one to expose the optic nerve and the other to expose the rest of the retina. In order to get the detail of the optic nerve, one could either reduce the output of the flash lamp or stop down the camera so that just this area is properly exposed to be able to see all the detail. However, by cutting down the flash power to be able to observe the optic nerve detail, one has insufficient light to be able to view the remainder of the retina. Note that with too high a strobe output the strobe saturates the camera due to the reflectivity of the optic nerve and all detail is gone.

As will be apparent, by raising the flash lamp power output one would simply see hotspots in the image for which detail is completely lacking.

In the past, in order to be able to view the detail of the retina away from the optic nerve, the typical practice was to slightly increase the flash lamp output which, while causing hotspots near the optic nerve or the pathology, it was possible to discern the detail of the darkened portion of the retina.

There is therefore a necessity for eliminating the requirement for multiple photographs, both from a patient comfort point of view and to be able to view all of the retina in a single image or photograph.

With the advent of digital cameras, usually having CCD sensor arrays of a 1- to 11-megapixel variety, it is possible to get real-time images of the retina. However, the problem of multiple pictures and flash lamp intensity versus optic nerve reflectivity has not as yet been resolved for the above reasons.

SUMMARY OF INVENTION

Rather than taking multiple exposures to obtain retinal and optic nerve detail, in the subject invention one exposure is used and a single image carries both optic nerve and dark retina detail. To make this possible, flash lamp intensity is lowered to avoid saturation and for obtaining optic nerve detail; and pixels viewing the low-intensity, now further darkened retinal regions have their outputs amplified so that the dark regions are brightened to reveal the detail. Note that the ability to see all aspects of the eye in one image or photograph aids diagnosis.

How this is accomplished is now described.

It will be appreciated that the pixels in a digital camera have outputs that are ascertainable. The dynamic range of each output is characterized by a grayscale having a range from 0 to 255, such that one can obtain 256 shades of any one color or gray. The grayscale in essence defines the dynamic range of the camera and to a certain extent the colors of the observed image.

In general, the outputs of each of the pixels of the array can be characterized by a transfer function that is linear, meaning a linear relationship between the input and the output. Normally this relationship of input to output is fixed and is dependent upon the characteristics of the digital camera.

Since each of the outputs of the CCD array of the digital camera is addressable, one can arrange to weight the individual outputs of individual pixels of the CCD array so as to increase the transfer function between input and output for those input levels or intensities that are relatively low.

Thus as one part of the subject invention, those pixels from the dark retina having a relatively low intensity have their outputs amplified to brighten those areas so that detail is visible. As a result, one can ascertain which of the pixels have relatively low outputs and multiply their inputs with a weight determined from a lookup table that will increase the output while not affecting the transfer functions for the pixels having higher outputs.

By increasing the outputs of the pixels having low-intensity inputs, one can obtain detail of the dark retinal area.

To obtain detail of the optic nerve and other highly reflective retinal objects, one first reduces flash lamp output to prevent saturation caused by reflections from the optic nerve or other highly reflective objects. Once having reduced the flash lamp output to avoid saturation one can view detail of the highly reflective retinal objects such as the optic nerve. However, reducing the flash lamp output further darkens the retina. With the subject technique the further darkened portions of the retina are brightened by the increased outputs for the low-output pixels. Thus both the optic nerve detail and the detail of the remainder of the retina are simultaneously viewable with one exposure in one picture. This solves the problems associated with multiple exposures.

The weighting function used, rather than being a linear weighting function, is alterable in one embodiment by utilizing a Bezier curve, the curvature of which is determined by four points, with two points being fixed and two points being variable. Given a Bezier curve to define the grayscale distribution, if one lowers the curve at the center portion to provide a belly, generally in the 220 to 240 grayscale range, then pixel outputs that are the result of the darker regions are increased.

In one embodiment the weighting system is user variable so that the user can move the belly of the curve up and down under the operator's control. This means that the operator can control the transfer function for all of the pixels, most notably the ones in the mid grayscale ranges corresponding to dark areas, simply by moving the variable points of the Bezier curve.

Thus what is done in the subject invention is to redistribute the grayscale values in a non-linear fashion along a curve so that the dark areas get bright while at the same time not significantly amplifying the outputs of those pixels that are detecting the high-reflectance optic nerve. The result is to be able to view the detail of the highly reflective materials in the eye while at the same time viewing the detail of the dark retina, and to do so with one exposure taking one picture.

The optimal nonlinear grayscale distribution takes the darker areas and makes the subtle details more exaggerated, while at the same time muting the changes in the lighter areas to produce a flattening effect.

Note that for the high-intensity pixels the transfer function mutes the amplification, thereby to mute the output. In short, for brighter light areas one is not transferring as much gain to the output for the particular pixel, whereas for the dark areas one is providing gain, with the weights specified by a look up table.

In one operating scenario, the first thing that one wants to do is to reduce the power of the flash lamp. The reason that one wants to reduce the power of the flash lamp is to limit the amount of reflection from the optic nerve. Thus one wants to get away from the situation where the reflection from the optic nerve saturates everything.

Then one adjusts the grayscale distribution to correct for the effect of the lowered flash lamp intensity on the darker regions of the retina by amplifying the output for low-intensity pixels, while at the same time leaving the transfer functions for the bright area pixels alone so that the transfer function for these pixels remains the same.

In summary, one cuts down the output of the flash lamp to eliminate gross saturation and then increases brightness of the dark regions or the low-intensity areas while at the same time keeping the others at the same level. This pops out the detail in both the darker regions and the bright regions.

It is possible to decrease the amplification for those pixels viewing darker regions to make the darker regions darker; but in so doing one would have a very high contrast effect, which is undesirable. The idea in color retinal imaging is not to create contrast but to balance it. Contrast is basically taking the dark regions and making them darker and taking the light regions and making them lighter.

In order to obtain a realistic view of the retina in terms of an image, one is trying to do just the opposite, namely trying to take everything and flatten the response out so that the image looks natural. This aids in the interpretation of the pathology of the retina so that what an ophthalmologist is looking at corresponds as nearly as possible to that which exists in nature. One in short does not want to create artificial conditions or artifacts that could in some sense make a diagnosis more difficult.

There is, however, another aspect to the use of the non-uniform grayscale distribution and that is to make the image available from the digital camera correspond to the images available from film. The reason that this is important is because many doctors are used to viewing film images in order to make diagnosis and would like to have the images that are available from the digital camera more closely correspond to what they are used to looking at.

By using the Bezier curve, which provides a polynomial fit between four points, and by adjusting the transfer function of each of the pixels based on the curve, one can adjust the curve to not only fix the problem of hotspots versus dark areas of a retina but also to correct the color response of the digital camera.

For each retinal camera, a model is generated to create what are called color planes or curves. These curves in essence describe the transfer function for each of the pixels in the camera. Since the color distribution curve is the composite of the red, green and blue response of the camera, by adjusting these curves one can make adjustments for each color. This is done by generating red, green and blue curves, altering them and then forming a color composite curve.

This is important to help compensate for flash temperatures. In general the output of a xenon flash strobe looks a little blue. One can correct to a realistic view by compensating for the blue illumination through adjusting the red and green response of the digital camera.

It is noted that film images tend to be very yellow when the images are obtained by illuminating the retina with a blue-shifted xenon output. This is because film in general is somewhat blue-muted. Thus when one takes photographs of the retina on film, they tend to have a slight yellow-orange look to them that might not necessarily be real but that which doctors are generally used to seeing.

In order to adjust the output of the CCD digital camera to provide yellow-orange, one wishes to make the output of these cameras look like what would be seen when using a film camera. One therefore actually seeks to mute the blue channel for the digital camera and can do so by generating weights from a nonlinear grayscale distribution.

Thus by using the Bezier curve and plugging in the red, green and blue characteristics of each color, one can make the images from the digital camera approximate that which would be seen utilizing a film camera and yet still be able to pop out the dark areas of the retina and the detail of the highly reflective retinal objects.

In summary, a system is provided to improve retinal camera picture quality by providing a user-variable transfer function for each pixel that results in redistributing grayscale values to solve the problem of saturation caused by highly reflective retinal objects. The result is the ability to capture both optic nerve and retina detail in a single picture. The darker retina is brightened using the redistributed grayscale values to permit observing retinal detail, while preserving optic nerve detail. The optic nerve and other highly reflective retinal objects are properly exposed by reducing flash lamp output to prevent saturation, while outputs of low-intensity pixels associated with the darker regions are intensified, in one embodiment in accordance with an adjustable Bezier curve. The result is that one can obtain retinal details previously flooded out by the reflections from the optic nerve while at the same time offering optic nerve detail. In one embodiment the redistributed grayscale values are optimized for each color plane to provide color-corrected images matching those associated with film cameras.

BRIEF DESCRIPTION OF THE DRAWINGS

These and other features of the subject invention will be better understood in connection with a Detailed Description, in conjunction with the Drawings, of which.

DETAILED DESCRIPTION

Figure 1:
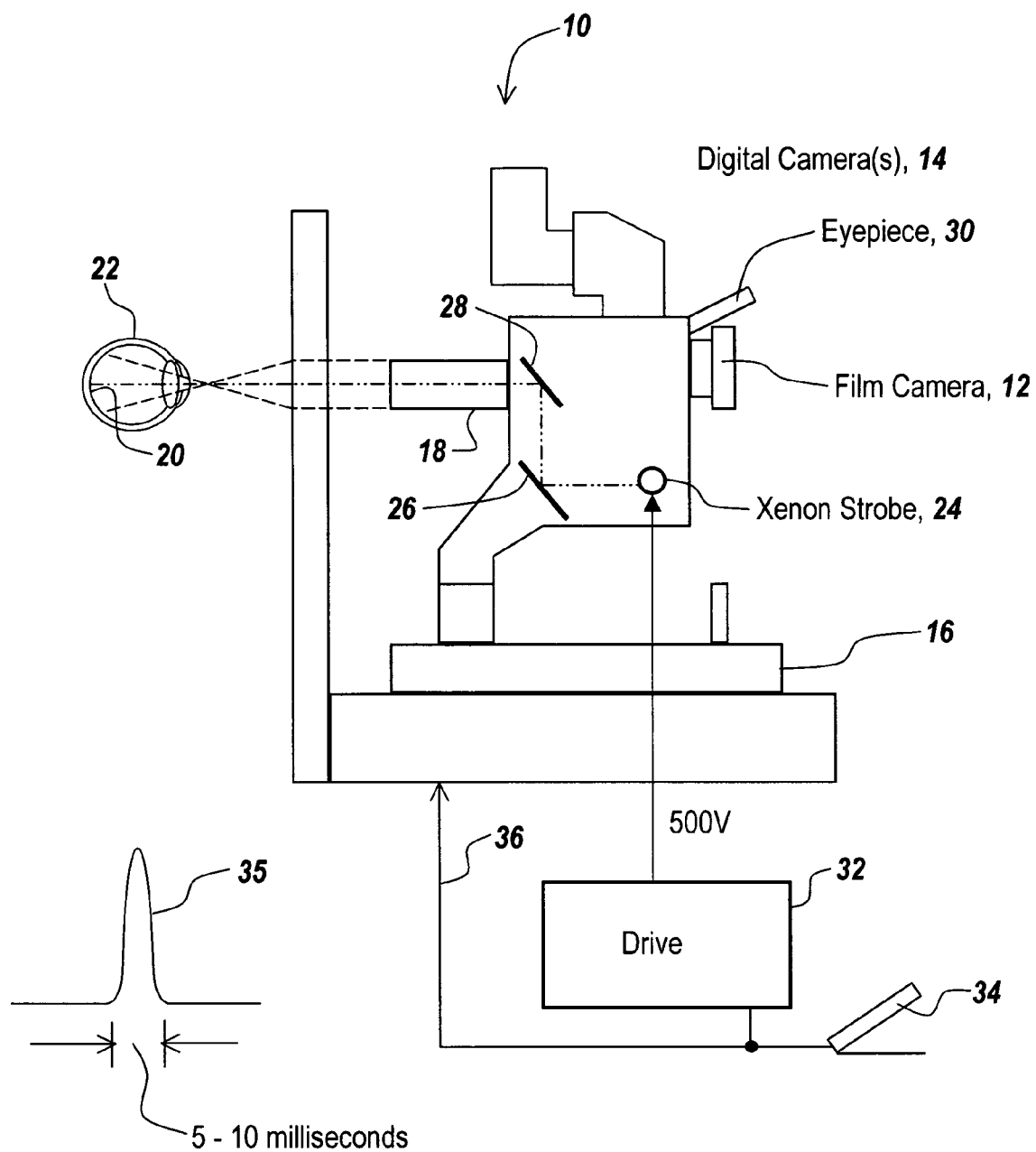
FIG. 1 is a diagrammatic illustration of a retinal camera, including a film camera, a digital camera, and drive for driving a strobe lamp so as to illuminate the retina of an eye.

Referring now to FIG. 1, prior to discussing the subject retinal image optimization system, the operation of a typical retinal camera is discussed. Here a retinal imaging camera 10 includes a film camera 12 and a digital camera 14 mounted on a stand 16 such that an imaging system 18 images the retina 20 of eye 22 onto the focal planes of cameras 12 and 14. In order to illuminate retina 20, a xenon strobe lamp 24 has its output redirected by mirrors 26 and 28 out through imaging system 18 so that the output of xenon strobe 24 illuminates retina 20. Note that an eyepiece 30 is used for focusing both the digital and film camera as well as directing the optics to the appropriate portion of the eye.

A precise maximum strobe output includes the use of drive 32 that incorporates a power supply for delivering several hundred volts to the xenon strobe. As illustrated, this is accomplished by delivery of a several hundred-volt pulse 35, with a pulse width of between 5 and 10 milliseconds. In one embodiment the strobe is activated by a foot switch 34.

It will be appreciated that foot switch 34 is also used to control camera 10 over line 36 to take the pictures such that any shuttering and exposure for either the film camera or the digital camera is controlled responsive to foot switch 34; or is actuated automatically if desired.

Figure 2:
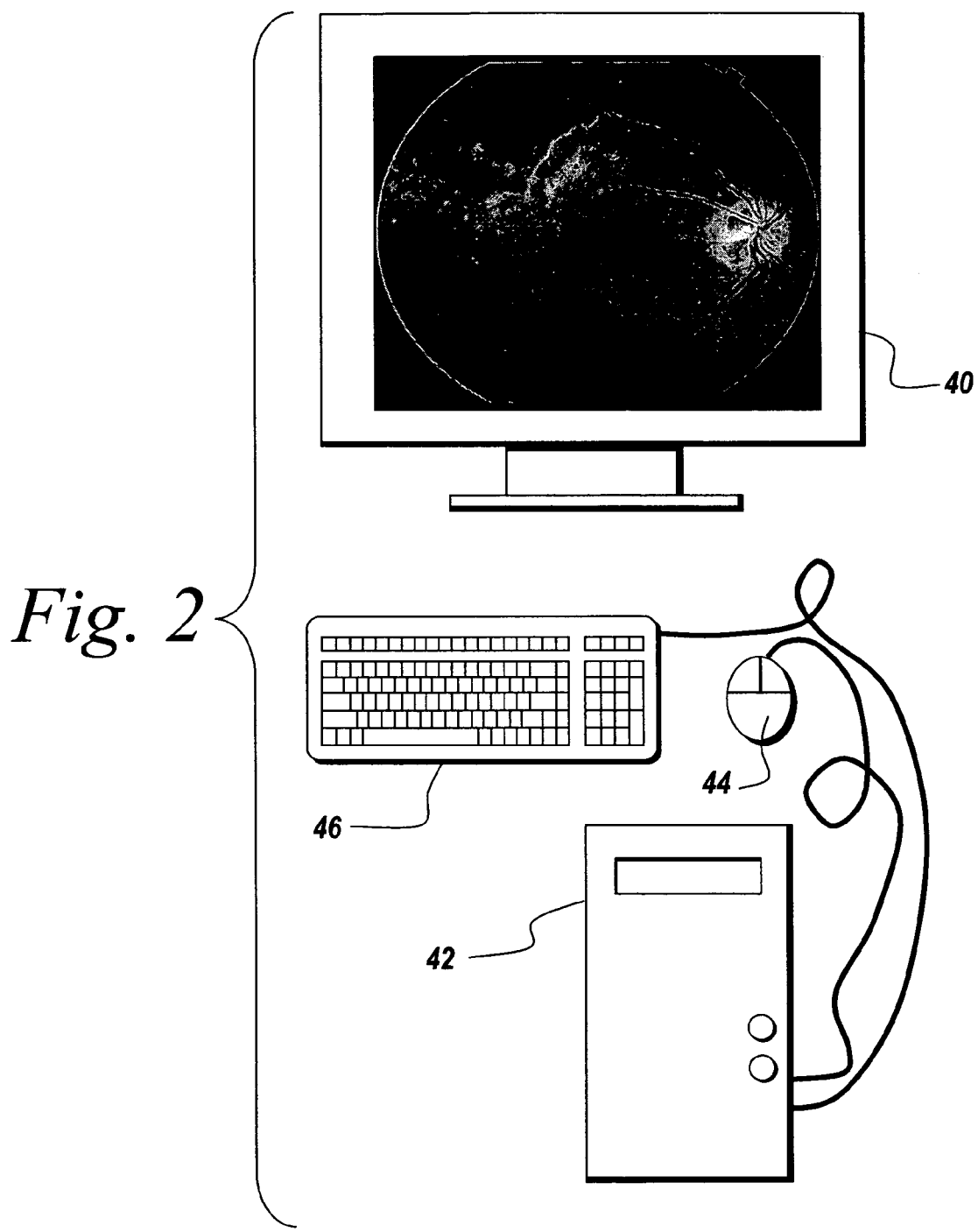
FIG. 2 is a diagrammatic illustration of a computer system used to weight the outputs of the CCD array in the digital camera of FIG. 1 so as to be able to output a single digital image containing detail of the retina and the optic nerve.

As illustrated in FIG. 2, a monitor 46 is used to display the retinal image as well as to display the aforementioned Bezier curves. Monitor 40 is coupled to a computer 42, with mouse 44 being used to specify the variable points of the Bezier curve. Note a keyboard 46 is used as a further input device.

Figure 3:
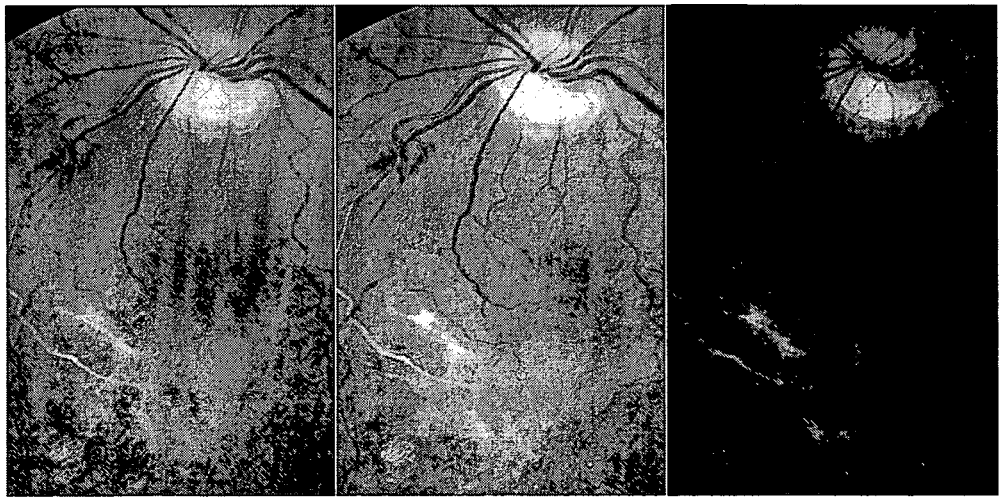
FIG. 3 is a series of images created by the digital camera of FIG. 1, illustrating an image of the retina showing a darkened image the result of reducing flash lamp output to eliminate saturation; an image using normal flash lamp outputs illustrating the saturation due to the reflections from the highly reflective optic nerve and other pathology; and am image showing the result of applying a nonlinear grayscale function to produce a compensated image in which retinal and optic nerve detail are obtained in one exposure.

Referring now to FIG. 3, activation of the xenon flash lamp of FIG. 1 results in an image of the retina along with the optic nerve attached. Note in the bottom photograph the retina is dark due to the lowering of the flash lamp output to eliminate saturation. While detail of some of the retina and the optic nerve can be seen, in general one must lighten up the dark retinal material in order to observe its features, and do so without causing saturation. The middle picture shows the result of using maximum flash lamp power. Here it can be seen that there are saturated areas that are completely whited out, thus destroying detail.

The upper picture shows a compensated image in which not only is the darker retinal area lightened to make retinal detail visible, the optic nerve detail is also visible.

The upper image is the result of applying a pixel weighting function. The weighting function affects the pixel transfer function by selectively amplifying the outputs of the low-intensity pixels. Here it can be seen that not only is the detail of the optic nerve observable, so also is the detail of the remainder of the retina, including all of the vascularization. It will be appreciated by the decreasing the flash lamp intensity to eliminate saturation coupled with the nonlinear grayscale weighting system that one can observe both the optic nerve detail and the detail of the darker surrounding retinal material in a single image. This aids diagnosis. An additional advantage is that only one photograph or one exposure per image need be made to obtain sufficient detail of all areas of the retina, thus limiting the pain associated with multiple exposures.

Figure 4:
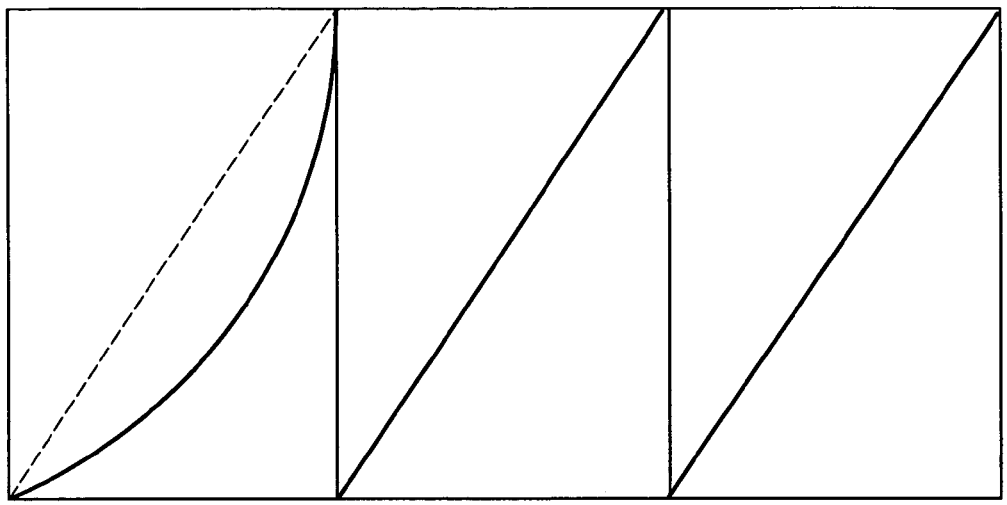
FIG. 4 is a series of graphs illustrating the control of the weights used in generating the images of FIG. 3, showing linear distribution for the dark and normal images and a Bezier curve defining the weights for the compensated image of FIG. 3.

Referring to FIG. 4, adjacent each of the dark, normal and compensated images is the corresponding curve that defines the weighting system used to weigh the outputs of the individual pixels. The lower and middle curves correspond to a linear distribution is used, meaning that for each pixel in the CCD array, its output is a fixed percentage of the input. This transfer function is the characteristic of the camera and is not altered.

However, the top graph shows a Bezier curve that defines the weights to be applied to the pixels.

Figure 5:
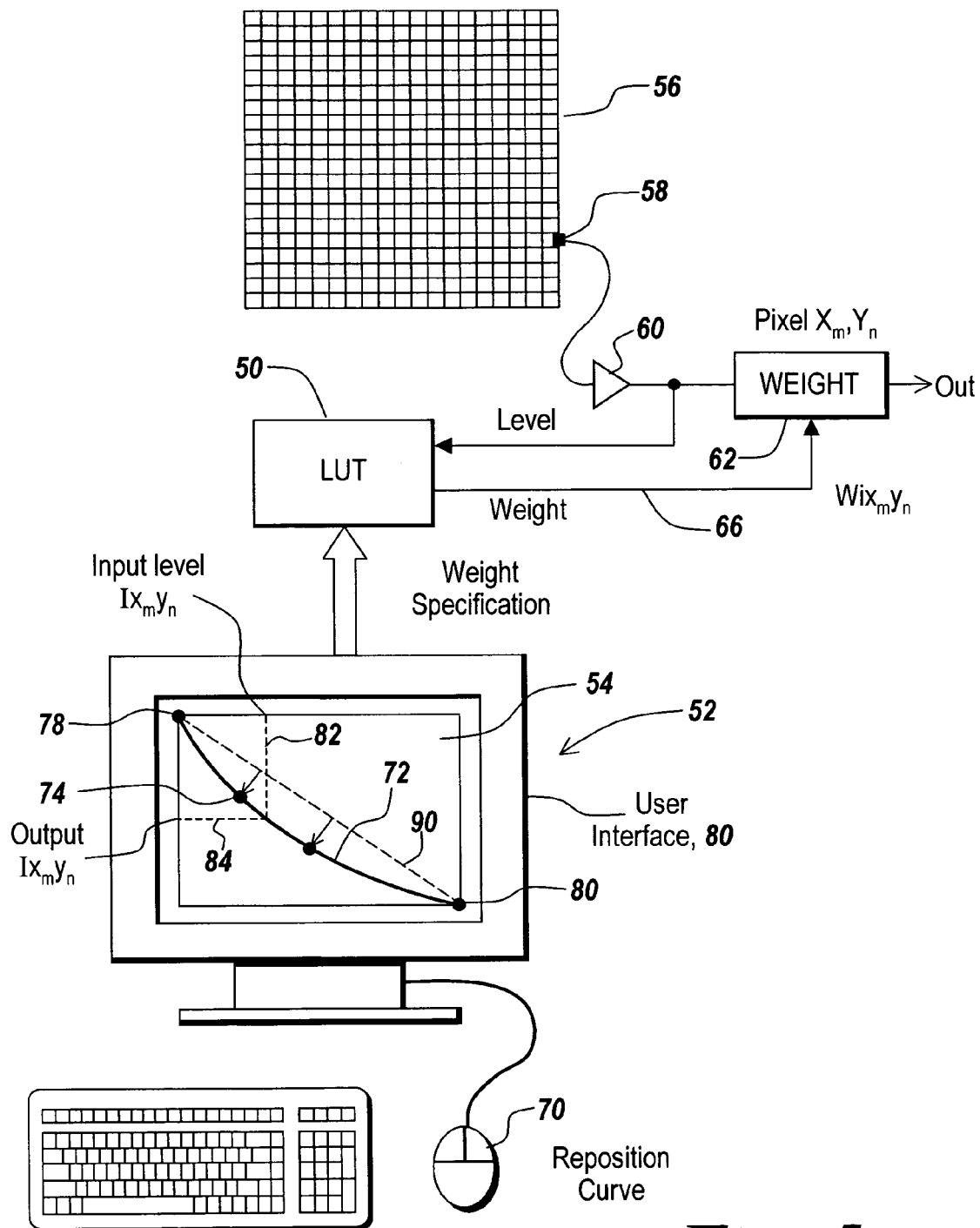
FIG. 5 is a diagrammatic illustration of the specification of weights in a look up table through manipulation of a Bezier curve, with the specification of the weights dependent upon the pixel output level.

Referring now to FIG. 5, how an individual pixel output is weighted is now described. Here it can be seen that the weights applied to a pixel are derived from a look up table 50 coupled to a computer 52. Look up table 50 is arranged to output a specified weight to be multiplied by the output of an addressed pixel, with the weight stored in the look up table being determined from the Bezier curve calculated by the computer.

The computer generates the Bezier curve on display 54, which for each of the 256 grayscale input levels determines an output level. Thus for a CCD array 56, a pixel 58, defined as pixel $X_m Y_n$, has its output amplified at 60, after which a weight is applied to its output by a weighting circuit 62.

The output of amplifier 60 is coupled to look up table 50 so that the initial level of the pixel can be ascertained. The look up table ascertains the grayscale input level for this pixel and ascertains the weight to be applied to the pixel output based on its input level. This weight is coupled over line 66 to unit 62 to apply a predetermined multiplication factor or weight to the output of amplifier 60. Alternatively, the table originally has values corresponding to a linear curve. The weighting is accomplished by reassigning the red value with the new y-intercept point on the curve.

As will be described, mouse 70 controls the curve 72 displayed at display 54 by in effect moving variable points 74 and 76, with points 78 and 80 being fixed. The line between the four points is generated using a Bernstein polynomial fit program such that the weights specified by look up table 50 can be controlled by user interface 80 comprised of computer 52, mouse 70 and display 54.

In the illustrated embodiment, an input level $Ix_m y_n$ is illustrated by dotted line 82, whereas the associated output level for such an input level is indicated by dotted line 84.

Figure 6:
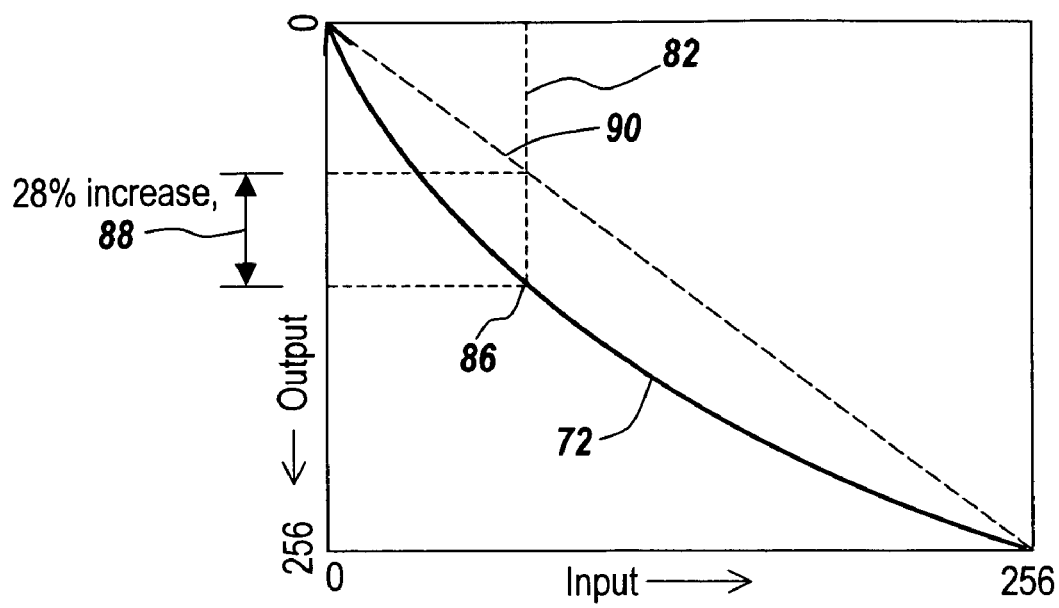
FIG. 6 is a graph showing that for a dimly illuminated pixel, moving the Bezier curve of FIG. 5 downwardly results in a 28% increase in the output, thus generating a weight of 1.28 by which the output of the associated pixel is multiplied.

Referring to FIG. 6, dotted line 82 intercepts Bezier curve 72 at point 86, which as illustrated by arrow 88 specifies a 28% increase in output over that which would have occurred if curve 72 were linear as illustrated at 90. Thus curve 72 specifies for an input illustrated by line 82 that there should be a 28% increase in the output for this particular pixel over that associated with a linear grayscale function.

Figure 7:
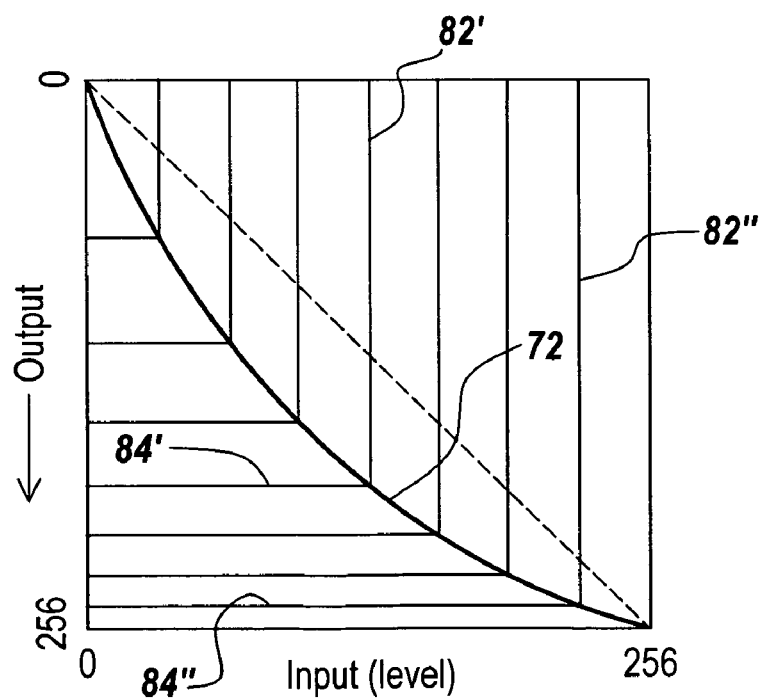
FIG. 7 is a graph of the Bezier curve of FIGS. 4, 5 and 6, illustrating that the Bezier curve defines pixel output level based on input level, with the Bezier curve defining the transfer function for the particular pixel.

Referring to FIG. 7, the graph shows the intersection with Bezier curve 72 of a number of different grayscale input levels illustrated by lines 82. In one embodiment, the grayscale is divided up into 256 levels. For each grayscale level there is an associated output. As can be seen from the low input levels at the mid range of the graph as illustrated at 82', the output at 84' is amplified over that specified by a linear relationship between input and output. Thus for the lower input levels the output associated with the particular pixel is highly amplified. However, for the higher input levels it will be seen that with the input level just below saturation as shown at 82", the output level is not significantly amplified. At this point the Bezier curve approximates a linear curve. How much the output for a given pixel input level is varied is therefore determined by the intersection of the input level with the Bezier curve.

Figure 8:
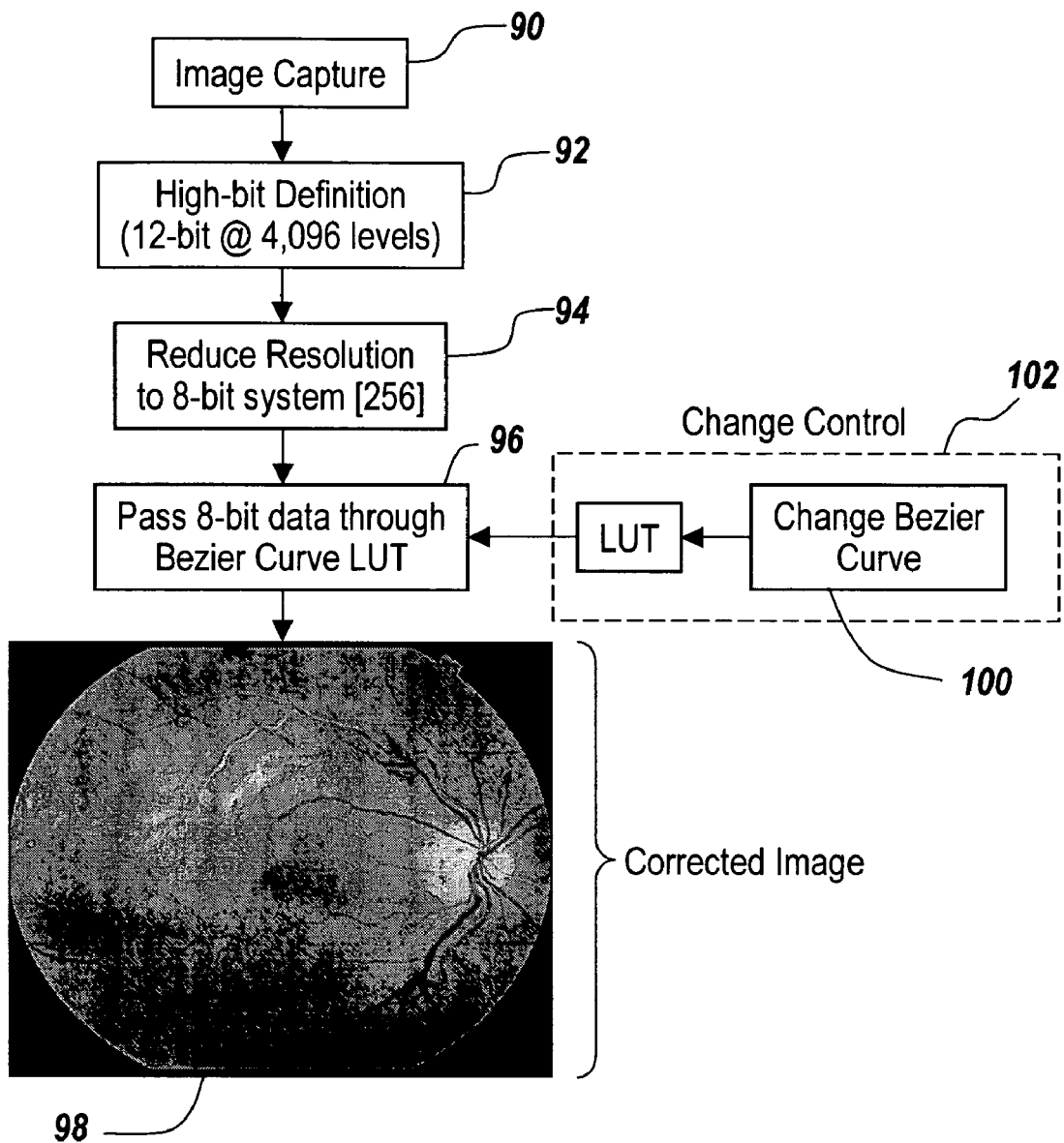
FIG. 8 is a flow chart showing the operation of the subject system from image capture through the production of a corrected image.

How this is accomplished is illustrated by the flowchart of FIG. 8 in which the image is captured as illustrated at 90. The capture is accomplished with high-bit definition as illustrated at 92 that involves 12 bits or 4,096 levels. This resolution is reduced as illustrated at 94 in one embodiment by conversion to an 8-bit system with 256 values. The resultant 8-bit values are passed through the Bezier curve look up table at 96 to produce image 98. This image is the corrected image, with the values for each pixel being multiplied by a weight determined by the look up table.

As can be seen, the look up table values can be changed as described above and as illustrated at 100, with the new values loaded into look up table 102.

Figure 9:
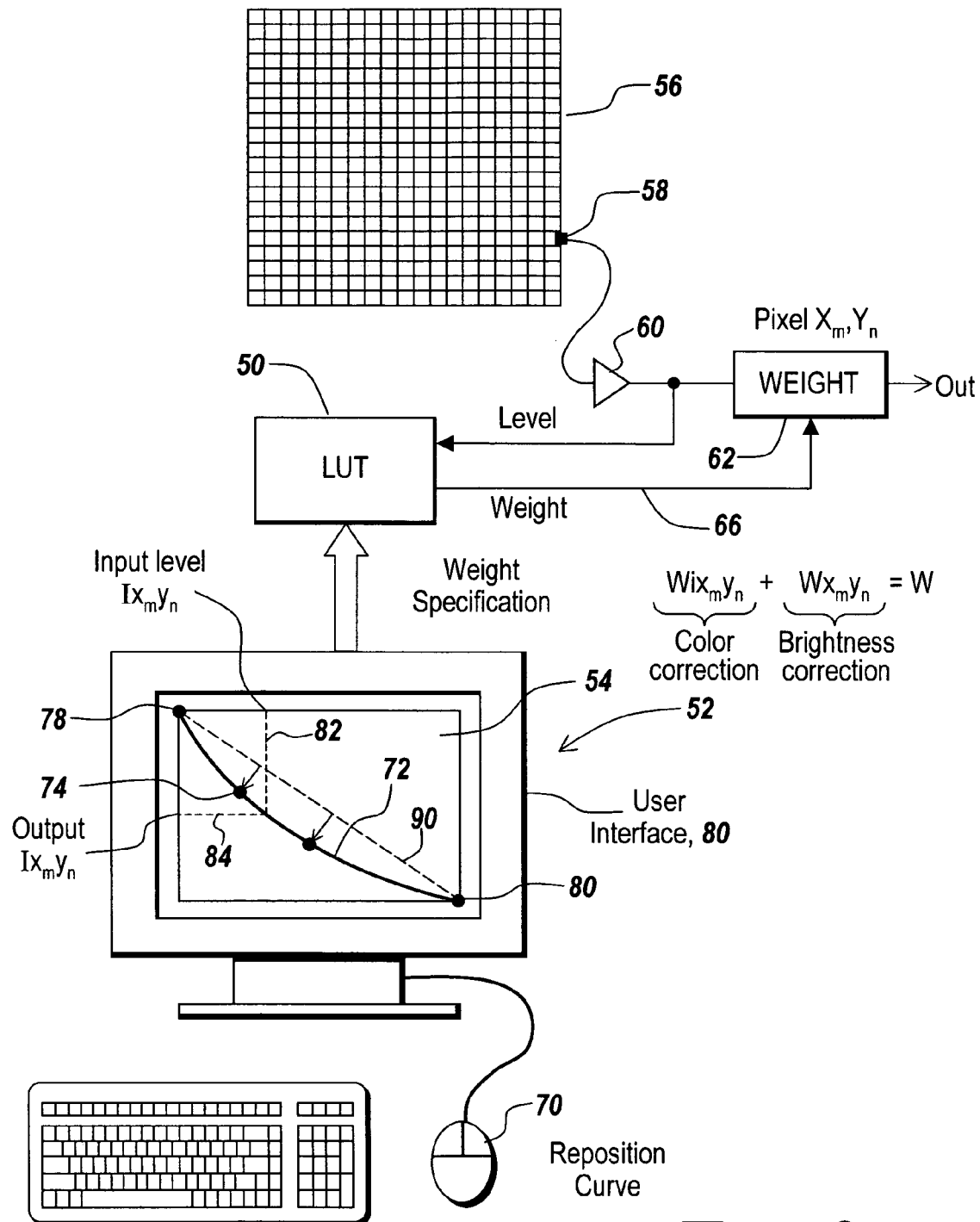
FIG. 9 is a diagrammatic illustration of the use of a non-linear grayscale distribution function to color-compensate a digital camera; and, FIG. 10 is a graph showing the Bezier curves for blue, green and red compensation and the resultant composite Bezier curve.

Referring now to FIG. 9 in which like elements between FIGS. 5 and 9 have like reference characters, it is possible to color-correct the digital camera using the subject system by adjusting the initial red, blue and green Bezier curves for blue color correction. The composite grayscale curve, being made up of the red, green and blue components, determines the color output of the camera and can be used to correct for the normal blue shift associated with xenon flash tubes.

In order to provide initial color correction, the weights generated by unit 62 include the color correction weights for each pixel, here $Wix_m y_n$. This refers to the initial color correction weights.

It will be appreciated that individual weights can be assigned to individual pixels to provide overall color correction. The composite Bezier curve permits tailoring or tweaking of the individual pixel outputs so as to provide improved color correction prior to correcting the overall image for brightness. Here it can be seen that the brightness correction weights, $Wx_m y_n$, are added to the color correction weights, $Wix_m y_n$, so that the weight generated for a given pixel is both the color corrected output for the pixel and the brightness correction output for the pixel.

Figure 10:
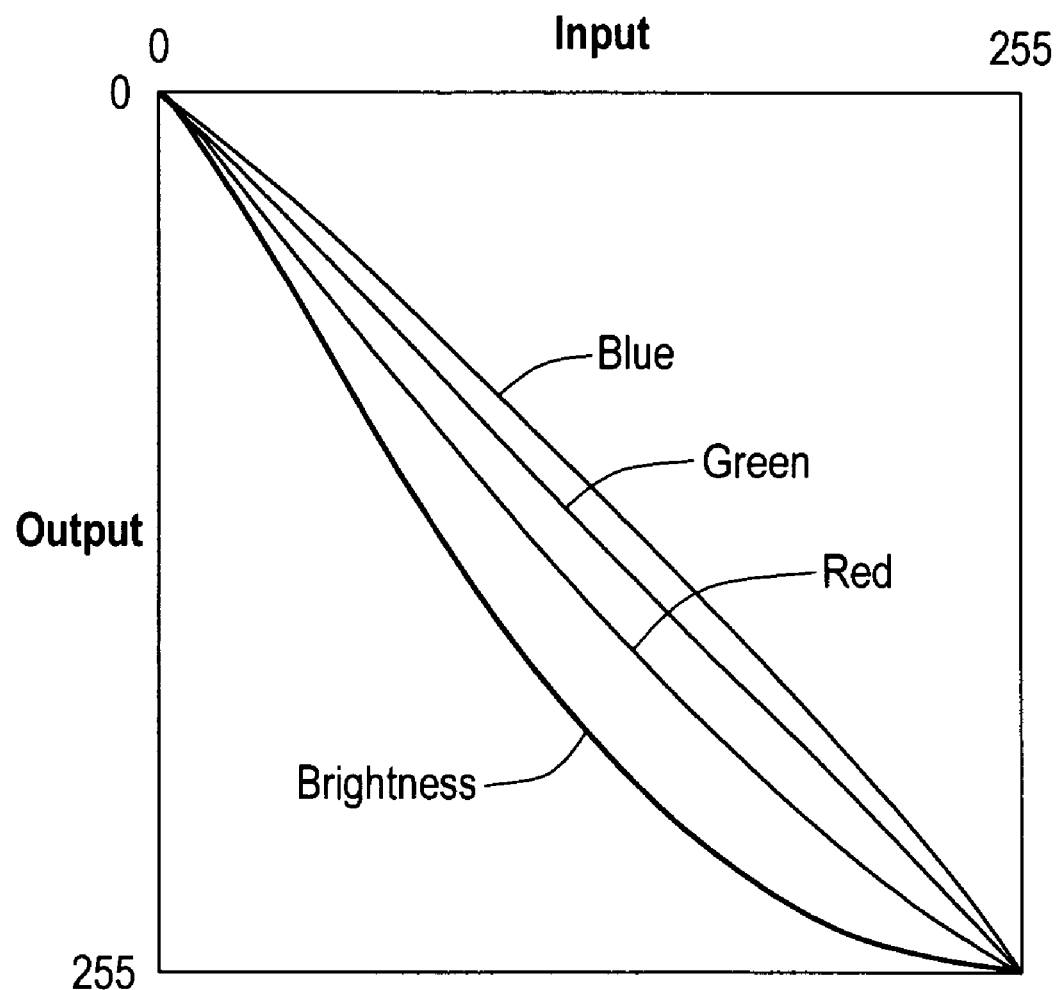

Referring to FIG. 10, it will be appreciated that for a given color camera one can generate blue, green and red Bezier curves which, when combined into a composite Bezier curve, weight the output of the pixels of the digital camera based on pixel intensity levels.

Put another way, these curves, generally defining so-called color planes, define the initial transfer function for each pixel based on input level. The color plane curves correct the image for the slightly blue tint of the xenon flash lamp.

The brightness compensation curve is applied after initial compensation to provide for the subject brightness control.

Also shown in this figure is the use of two variable Bezier points to generate the blue curve. Thus it can be seen that the three curves can be specified by two fixed points and two variable points, although more flexible points can be added if desired.

Thus one can weight the outputs of the pixels based on input levels to be able to select the lower illuminated pixels and to heavily amplify their outputs while only slightly amplifying high-intensity pixels. The result is a flattening that permits viewing detail not only in the dark retinal areas, but also detail in the highly reflective regions; and to do so with only one exposure in a single image or picture.

A program listing in C follows describing the generation of the Bezier curve, the operation of the look up table and the generation of the weights required to provide the corrected image.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. In a digital retinal camera having a sensor including an array of pixel elements, a method for improving retinal imaging for retinal images degraded by saturation due to highly reflective retinal objects, comprising the steps of:
adjusting the flash lamp output of the retinal camera to a point at which the detail of highly reflective retinal objects is observable; and,
amplifying the returns from non-highly reflective retinal objects to brighten them to an extent that the detail of the non-highly reflective retinal objects is observable, whereby both highly reflective and non-highly reflective retinal objects are observable in one image, thereby eliminating the requirement for multiple exposures to obtain retinal image detail.

2. The method of claim 1, wherein the amplification for the non-highly reflective retinal objects includes the use of a user-variable transfer function that applies weights to the outputs of the sensor array elements in the retinal camera that result in a redistributed grayscale.

3. The method of claim 2, wherein the user-variable transfer function defines weights tailored for each pixel.

4. The method of claim 3, wherein the user-variable transfer function is defined by a variation from a linear transfer function.

5. The method of claim 4, wherein the weight for each pixel is determined by an adjustable Bezier curve having a curvature specified by the user.

6. The method of claim 1, wherein the amplification for each pixel is determined by associated transfer function weights.

7. The method of claim 6, wherein the transfer function weight for each pixel is determined by a look up table.

8. The method of claim 7, wherein the weights stored in the look up table include values determined by the user.

9. The method of claim 8, wherein one input to the look up table includes the intensity level of a pixel and wherein the look up table outputs the weight associated with the input intensity level of the associated pixel.

10. The method of claim 9, wherein the weight outputted by the look up table is that associated with a user-defined Bezier curve.

11. The method of claim 1, and further including the step of color-correcting images from the digital camera by initially specifying transfer function weights for each pixel level in terms of a grayscale distribution to color shift the images associated with the digital camera to match those expected from film cameras.

12. The method of claim 1, wherein specifying the transfer function for each pixel results in redistributing the associated grayscale values.

13. A grayscale redistribution system for improving retinal imaging from a digital camera including an array of sensor elements, each defining a pixel, to permit capture of the digital image in one exposure so as to reveal detail of both highly reflective retinal objects and non-highly reflective retinal objects in one image, comprising:
a system for weighting the outputs of individual pixels in accordance with the output level of a pixel so as to amplify the output of those pixels viewing darker retinal regions.

14. The system of claim 13, and further including a look up table for specifying the weights provided by said weighting system.

15. The system of claim 14, wherein the weight specified by said look up table is defined by the intersection of the pixel output level with a curve, whereby the output of a predetermined pixel is weighted by said intersection.

16. The system of claim 15, wherein said curve includes a Bezier curve.

17. The system of claim 16, wherein said Bezier curve is determined by two fixed points and lies below a straight line between said two fixed points, said straight line defining a linear curve.

18. The system of claim 17, wherein said Bezier curve is user controllable.

19. The system of claim 18, wherein the weights specified by said look up table include an amplification component and a color correction component, said color correction component being derived from the composite of color plane curves, said color plane curves being altered to correct the retinal image from said digital camera to more closely correspond to the retinal image one would expect from a film camera.

20. A method for providing a retinal image from a digital retinal camera employing a flash lamp so as to make viewable detail of both highly reflective retinal objects and non-highly reflective retinal objects in a single exposure, comprising the steps of:
reducing the flash lamp output to a point at which detail of highly reflective retinal objects is viewable in the image produced by the digital camera; and,
redistributing the camera grayscale to amplify pixel outputs associated with non-highly reflective retinal objects to a point where they are viewable, whereby an image having sufficient detail in all retinal areas can be made of the retina in one exposure, thus to eliminate multiple exposures of the eye while at the same time rendering retinal detail of both highly reflective and non-highly reflective retinal objects in a single image for improved diagnostic purposes.

21. The method of claim 20, wherein the clarification of the non-highly reflective retinal objects to permit viewing the detail thereof which has been darkened due to the reduction of the flash lamp output is user controllable.

22. The method of claim 20, wherein the redistributed grayscale includes a redistribution that also color corrects the retinal image so that it more closely approximates an image that would be available from a film camera.

23. A method for minimizing exposure of a patient to high-intensity strobe flashes of a retinal camera when taking pictures of the retina, comprising the step of:
generating a retinal image in a single exposure that presents detail of both highly reflective retinal objects and non-highly reflective retinal objects in a single picture.

24. The method of claim 23, wherein the step of rendering a single image having retinal detail includes redistributing the grayscale associated with the retinal camera so as to amplify the outputs of pixels in the retinal camera viewing dark areas of the retina more than those pixels viewing highly reflective retinal objects.

* * * * *